US006333427B1

(12) United States Patent
Miyake et al.

(10) Patent No.: US 6,333,427 B1
(45) Date of Patent: Dec. 25, 2001

(54) PROCESS FOR PREPARING N-T-BUTOXYCARBONYLPHENYLALANINE ESTER

(75) Inventors: Hitoki Miyake; Masami Osabe, both of Chiba; Mitsuo Koito, Fukuoka; Setsuo Yoshino, Aichi; Nobuhiro Fukuhara, Fukuoka, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/507,676

(22) Filed: Feb. 22, 2000

(30) Foreign Application Priority Data

Feb. 23, 1999 (JP) .................................. 11-044484
Mar. 19, 1999 (JP) .................................. 11-074703

(51) Int. Cl.[7] .............................................. C07C 229/00
(52) U.S. Cl. ............................................. 560/41; 560/40
(58) Field of Search ....................... 560/40, 41; 562/401

(56) References Cited

U.S. PATENT DOCUMENTS 3,839,396 10/1974 Otsuka .

FOREIGN PATENT DOCUMENTS 2234798 1/1973 (DE) .
1166403 * 10/1969 (GB) .
49133301 12/1974 (JP) .

OTHER PUBLICATIONS

Caplus abstract of JP 1130244 A2. Oshiki et al. Separation of N–hydrocarbyloxycarbonyl)amino acid esters.*
Derwent Abstract (1995–093819) of JP 2801500 (1995), Preparation of N–alkoxy–carbonyl amino acid used for mfg. antibiotics etc.–by contacting N–alkoxycarbonyl aminacid aq. solution of suspension with organic solvent, sepg. orgaqnic phase and dehydrating.*
Derwent Abstract (1995–242658) of JP 07145136 A (1995). N–alkoxycarbonyl ester prepn. in high yield–by forming aminoacid ester sulphate from aminoacid, olefin and sulfuric acid, neutralizing and reacting with carbonate.*
Derwent Abstract (1992–238148) of JP 04159296 A. Purifcn. of N–(t–butoxycarbonyl) alpha–L–aspartyl l–phenylalanien methyl ester–by treating with aromatic hydrocarbon.*

* cited by examiner

Primary Examiner—Paul J. Killos
Assistant Examiner—Mahreen Chaudhry
(74) Attorney, Agent, or Firm—Burns, Doane, Swecker & Mathis L.L.P.

(57) ABSTRACT

A purified N-t-butoxycarbonylphenylalanine ester preparation having an enhanced optical activity can be obtained by bringing an N-t-butoxycarbonylphenylalanine ester preparation containing an optically active compound into contact with an aliphatic hydrocarbon, extracting the optically active compound with the aliphatic hydrocarbon, and recovering the optically active compound from the resulting extract.

8 Claims, No Drawings

PROCESS FOR PREPARING N-T-BUTOXYCARBONYLPHENYLALANINE ESTER

FIELD OF THE INVENTION

The present invention relates to a process for purifying an optically active N-t-butoxycarbonylphenylalanine ester used widely as a pharmaceutical intermediate, and a process for preparing an optically active N-t-butoxycarbonylphenylalanine ester, including said purification process.

DESCRIPTION OF THE RELATED ART

As a process for preparing an N-t-butoxycarbonylphenylalanine ester, a process including reaction of an amino group of an optically active phenylalanine ester with a t-butoxycarbonylating agent (BOC agent) such as di-t-butyl dicarbonate hitherto is known. For example, a process using reaction of a phenylalalanine ester hydrochloride with di-t-butyl dicarbonate in an organic solvent in the presence of an inorganic base such as potassium carbonate is known (Japanese Patent Laid-Open (Kokai) No. 233138/95). According to this process, an N-t-butoxycarbonylphenylalanine ester preparation retaining a high optical purity can be prepared.

However, when the BOC agent is industrially prepared, since this process causes problems on the reaction and operation, the BOC agent can not be prepared at a low cost. Therefore, this process using the BOC agent is considered to be not economical. In addition, when the optical purity of the optically active phenylalanine ester preparation as a starting material is low, the optical purity of the desired final product is also low.

On the other hand, a process for preparing an N-t-butoxycarbonylphenylalanine ester at a low cost is known (Japanese Patent Laid-Open (Kokai) No. 133301/74), in which an N-carbonylphenylalanine ester is obtained from a phenylalanine ester hydrochloride and phosgene, and, then, reacted with t-butanol in the presence of a tin compound such as dibutyltin dichloride to obtain the N-t-butoxycarbonylphenylalanine ester.

However, since the reaction between an amino acid ester and phosgene is generally effected at high temperature of 100° C. or higher, the optical purity of the reaction product is often lowered. As a result, the N-t-butoxycarbonylamino acid ester obtained by reacting the N-carbonylphenylalanine ester with t-butanol can not always have a high optical purity. According to the present inventors' knowledge, the N-carbonyl-L-phenylalanine methyl ester obtained by the above technique through the reaction using the phenylalanine ester hydrochloride and phosgene has no satisfactory optical purity because of racemization during the reaction.

As a general process for purifying an N-t-butoxycarbonylphenylalanine ester, there is a process for extracting an N-t-butoxycarbonylphenylalanine ester with an organic solvent such as dichloromethane. However, any knowledge with respect to an optical purity of an N-t-butoxycarbonylphenylalanine ester in these purification processes has never been obtained.

The N-t-butoxycarbonylphenylalanine ester, in particular the N-t-butoxycarbonylphenylalanine ester, wherein phenylalanine is L-phenylalanine and an ester is a methyl ester is expected to be used as an intermediate of a drug for treatment of HIV. Thus, it has been required to develop a product having a high optical purity and an industrially low production cost.

SUMMARY OF THE INVENTION

An object of the present invention is to provide an industrially advantageous process for purifying an N-t-butoxycarbonylphenylalanine ester preparation to improve its optical purity. Another object of the present invention is to provide an industrially advantageous process for producing an N-t-butoxycarbonylphenylalanine ester preparation with a high optical purity using the above purification process. Another object of the present invention is to provide a process for producing a N-t-butoxycarbonylphenylalanine ester preparation with a low production cost.

To achieve the above objects, the present inventors have studied intensively so as to obtain an N-t-butoxycarbonylphenylalanine ester preparation having a high optical purity. As a result, they have found that the racemic compound of the N-t-butoxycarbonylphenylalanine ester hardly dissolves in an aliphatic hydrocarbon, however, the optically active form thereof sufficiently dissolves in the aliphatic hydrocarbon and, therefore, only the optically active form of the N-t-butoxycarbonylphenylalanine ester can be efficiently extracted with the aliphatic hydrocarbon. Thus, the present invention has been completed.

The process for purifying an N-t-butoxycarbonylphenylalanine ester according to the present invention is a purification process for improving an optical purity of an N-t-butoxycarbonylphenylalanine ester preparation, which comprises the steps of:

bringing a crude preparation containing an optically active form of an N-t-butoxycarbonylphenylalanine ester into contact with an aliphatic hydrocarbon, and extracting the optically active form in the crude preparation into the aliphatic hydrocarbon to prepare an extract; and recovering the optically active form from the extract to obtain a purified N-t-butoxycarbonylphenylalanine ester preparation having an improved optical activity.

The process for preparing an N-t-butoxycarbonylphenylalanine ester according to the present invention is a process for preparing an optically pure N-t-butoxycarbonylphenylalanine ester preparation, which comprises the following steps (1) to (3) of:

(1) reacting a phenylalanine ester salt with phosgene in an organic solvent, thereby to introduce a carbonyl group into an amino group of the phenylalanine ester to prepare an N-carbonylphenylalanine ester;

(2) reacting the N-carbonylphenylalanine ester obtained in the step (1) with t-butanol to prepare a crude N-t-butoxycarbonylphenylalanine ester preparation; and (3) bringing the crude N-t-butoxycarbonylphenylalanine ester preparation obtained in the step (2) into contact with an aliphatic hydrocarbon, extracting an optically active form of the N-t-butoxycarbonylphenylalanine ester into the aliphatic hydrocarbon, and recovering the optically active form from the resulting extract to obtain a purified N-t-butoxycarbonylphenylalanine ester preparation containing the optical active form with an improved optical purity.

According to the present invention, an N-t-butoxycarbonylphenylalanine ester preparation can be purified by a simple purification process comprising the step of extracting the optically active form of an N-t-butoxycarbonylphenylalanine ester into an aliphatic hydrocarbon. Furthermore, the N-t-butoxycarbonylphenylalanine ester preparation having a high optical purity can be efficiently prepared by the above simple purification process.

When the ester to be purified is obtained from a phenylalanine ester salt via phosgenation and butoxycarbonylation, an N-t-butoxycarbonylphenylalanine ester preparation with a high optical purity can be efficiently produced with a low production cost.

DETAILED DESCRIPTION OF THE INVENTION AND PREFERRED EMBODIMENTS

A crude preparation of an N-t-butoxycarbonylphenylalanine ester used in the purification process according the present invention contains an optically active form of the N-t-butoxycarbonylphenylalanine ester, and examples thereof include a preparation comprising a mixture of the optically active form and the racemic form of the N-t-butoxycarbonylphenylalanine ester. The N-t-butoxycarbonylphenylalanine ester preparation, to which the purification process of the present invention can be applied, may be those prepared by any known preparation process. As the preparation process, for example, a process for preparing an N-t-butoxycarbonylphenylalanine ester via an N-carbonylphenylalanine ester is industrially advantageous because of its low production cost.

When the N-t-butoxycarbonylphenylalanine ester is produced by a process using reaction by BOC agent and its optical purity is low, the optical purity can be also increased by the purification process according to the present invention.

As described hereinafter, the N-carbonylphenylalanine ester can be easily synthesized from a phenylalanine ester hydrochloride and phosgene by a conventional procedure, and the resulting N-carbonylphenylalanine ester can be isolated from the reaction solution by distillation. Next, the N-t-butoxycarbonylphenylalanine ester is formed by reacting the N-carbonylphenylalanine ester with t-butanol and the product thus obtained can be used in the purification process according to present invention. In the reaction between the N-carbonylphenylalanine ester and t-butanol, a known catalyst such as organic base, tin compound or the like may be added.

As the ester group constituting the ester with N-t-butoxycarbonylphenylalanine in the present invention, for example, an alkyl group, an alkenyl group or an aralkyl group can be used without being limited. Among these groups, a lower alkyl group having 1 to 4 carbon atoms, such as a methyl, ethyl, n-propyl, isopropyl, n-butyl, or t-butyl group is preferably used. A methyl group or an ethyl group is particularly preferred.

The aliphatic hydrocarbons are used in the present invention, in which the racemic form of the N-t-butoxycarbonylphenylalanine ester can not dissolve, while the optically active form can be dissolved. Preferred examples thereof include n-pentane, n-hexane, methyldiethylethane, dimethylpropylmethane, dimethylisopropylmethane, trimethylethylmethane, cyclohexane, n-heptane, and n-octane. These aliphatic hydrocarbons may be used alone, or two or more kinds of them may be used in combination.

Regarding selction of the aliphatic hydrocarbons, those in which the racemic form does not dissolved or in which the solubility of the racemic form is so low so as to obtain the increased optical purity as desired in the resultant purified preparation.

The amount of the aliphatic hydrocarbon to be used is not specifically limited, but is preferably an amount enough to dissolve the total amount of the optically active form of the N-t-butoxycarbonylphenylalanine ester to be used. Specifically, the amount of the aliphatic hydrocarbon is preferably 2 to 20 times, more preferably 5 to 10 times, larger than the amount of the N-t-butoxycarbonylphenylalanine ester on the weight basis.

The extraction temperature may be lower than the melting point of the racemic form of N-t-butoxycarbonylphenylalanine ester, and ranges usually from the solidification point of the aliphatic hydrocarbon to 60° C., and preferably from 0 to 30° C.

In the present invention, the racemic N-t-butoxycarbonylphenylalanine ester, which is deposited as a crystal form by extraction of the optically active N-t-butoxycarbonylphenylalanine ester with the aliphatic hydrocarbon, can be separated by a known procedure such as filtration, centrifugal separation or the like. To recover the optical active N-t-butoxycarbonylphenylalanine ester from the aliphatic hydrocarbon solution, the aliphatic hydrocarbon can be removed by a simple procedure such as distillation under reduced pressure.

The procedure including the extraction using the aliphatic hydrocarbon may be repeated in order to further improve the optical purity of the N-t-butoxycarbonylphenylalanine ester preparation.

One embodiment of the preparation of the N-t-butoxycarbonylphenylalanine ester having a high optical purity in the present invention will be described in detail hereinafter.

The N-carbonylphenylalanine ester can be easily prepared, for example, from a phenylalanine ester salt and phosgene by a conventional procedure. Specifically, it can be prepared by a process comprising the steps of suspending a phenylalanine methyl ester hydrochloride in toluene and bubbling phosgene into the suspension, as described in Japanese Patent Laid-Open (Kokai) No. 29755/73.

As an ester group constituting the phenylalanine ester in the preparation, for example, an alkyl group, an alkenyl group or an aralkyl group can be used without being limited. Among these groups, a lower alkyl group having 1 to 4 carbon atoms, such as a methyl, ethyl, n-propyl, isopropyl, n-butyl, or t-butyl group is preferably used. A methyl group or an ethyl group is particularly preferred.

The organic solvent for the phosgenation reaction includes, for example, aromatic compound such as toluene and xylene; halide such as chloroform and dichloromethane; and acetate such as ethyl acetate, methyl acetate and butyl acetate. Two or more kinds of these organic solvents can be used in combination. The amount of the organic solvent is not specifically limited, and ranges preferably from 2 to 20 times, more preferably from 5 to 10 times, larger than the amount of the phenylalanine ester on the weight basis.

The amount of phosgene to be used in the present invention ranges preferably from 1 to 20 mol, particularly 2 to 10 mol, relative to one mol of the phenylalanine ester. The bubbling rate of phosgene is not specifically limited, but is preferably 0.1 to 1 mol, relative to one mol of the phenylalanine ester, per one hour. Both of the amount and bubbling rate of phosgene may exceeds the above range, but excess bubbling is not economical.

The reaction temperature of the phosgenation in the present invention may be any temperature at which the reaction proceeds, and is within a range from 10° C. to the boiling point or lower of the reaction solution, preferably from 60 to 120° C.

After the completion of the phosgenation reaction, excess phosgene is removed from the reaction system by using an inert gas such as nitrogen. Subsequently, the reaction solvent is distilled off under reduced pressure or normal pressure, thereby making it possible to obtain an oily N-carbonylphenylalanine ester preparation.

The oily N-carbonylphenylalanine ester preparation formed by the phosgenation reaction can also be purified from the reaction solution by distillation according to a conventional procedure to remove impurities or tar formed during the phosgenation reaction. For example, Japanese Laid-Open (Kokai) No. 54002/73 discloses an example of subjecting the N-carbonylphenylalanine ester to vacuum distillation under the conditions of 145–147° C./1.6 kPa.

The crude N-carbonylphenylalanine ester can be prepared by reacting the oily N-carbonylphenylalanine ester with excess t-butanol under heating.

The amount of t-butanol to be used in the present invention is not specifically limited as far as it is an equimolar amount or higher, relative to the amount of the N-carbonylphenylalanine ester.

The temperature of the reaction between the N-carbonylphenylalanine ester and t-butanol is not specifically limited as far as the reaction proceeds, and ranges preferably from 40° C. to the reflux temperature of t-butanol, and the reflux temperature of t-butanol is more preferable.

In the reaction between the N-carbonylphenylalanine ester and t-butanol, a known catalyst such as organic base, tin compound or the like may be added.

The N-carbonylphenylalanine ester can be purified by extracting the crude N-carbonylphenylalanine ester, which is obtained by reacting the N-carbonylphenylalanine ester with t-butanol, with an aliphatic hydrocarbon. In this purification, the above-described purification process can be employed.

EXAMPLE 1

To 19.4 g of an oily N-t-butoxycarbonyl-L-phenylalanine methyl ester preparation having an optical purity of 97.5%ee, 174.0 g of hexane was added, followed by uniform dispersion. As a result, crystals containing the racemic form were precipitated. After the suspension containing the crystals was stirred at 20° C. for one hour, the crystal was removed by filtration. The filtrate was concentrated under reduced pressure to obtain 18.5 g of an N-t-butoxycarbonyl-L-phenylalanine methyl ester. Analysis revealed that the optical purity is 99.5%ee. Subsequent analysis revealed that the optical purity of the removed crystals containing the racemic form is 46.4%ee. It is, therefore, clear that optical resolution was attained by extraction.

EXAMPLE 2

To 1.0 g of an N-t-butoxycarbonyl-L-phenylalanine methyl ester preparation having an optical purity of 97.5%ee, 9.0 g of each of the aliphatic hydrocarbons shown in Table 1 was added individually. After stirring at 25° C. for one hour, crystals were removed by filtration. The optical purity of the N-t-butoxycarbonyl-L-phenylalanine methyl ester preparation recovered from the filtrate in the same manner as in Example 1 was determined and compared with that before this purification procedure by a treatment using an aliphatic hydrocarbon. The results are shown in Table 1.

TABLE 1

| Aliphatic hydrocarbon | Cyclohexane | n-heptane | n-octane |
| --- | --- | --- | --- |
| Before purification | 97.5% ee | 97.5% ee | 97.5% ee |
| After purification | 99.0% ee | 99.8% ee | 99.8% ee |

EXAMPLE 3

To 2.8 g of an N-t-butoxycarbonyl-L-phenylalanine ethyl ester preparation having an optical purity of 93.4%ee, 9.5 g of n-hexane was added. After stirring at 2° C. for one hour, crystals were removed by filtration. The optical purity of the N-t-butoxycarbonyl-L-phenylalanine ethyl ester preparation recovered from the resulting filtrate in the same manner as in Example 1 was determined by analysis. As a result, it was 99.3%ee.

EXAMPLE 4

98.7 g (383 mmol) of a L-phenylalanine methyl ester was dissolved in 351.8 g of toluene and then a hydrochloric acid gas was bubbled into the solution at room temperature in a rate of 20 g/hour to obtain a slurry solution of a L-phenylalanine methyl ester hydrochloride. After the slurry solution was heated to 110° C., the reaction was conducted for 2.5 hours while bubbling a phosgene gas into the slurry solution at a rate of 30 g/hour. After the completion of the reaction, a nitrogen gas was bubbled into the reaction solution at 110° C. at a rate of 45 L/hour for two hours and excess phosgene gas was removed from the reaction system. Toluene was distilled off at 40° C. under reduced pressure from the reaction solution to obtain 84.8 g of an unpurified oily N-carbonyl-L-phenylalanine methyl ester preparation. The purity of the unpurified N-carbonyl-L-phenylalanine methyl ester preparation was 90.2% and the reaction yield was 96.9%.

A fraction at 150–152° C. was recovered under 1.4 kPa from 84.4 g of the unpurified N-carbonyl-L-phenylalanine methyl ester preparation by single distillation, thereby to isolate 60.9 g of N-carbonyl-L-phenylalanine methyl ester preparation.

To 60.9 g of the N-carbonyl-L-phenylalanine methyl ester, 66.0 g of t-butanol was added and the reaction was conducted under reflux for eight hours. Then, the unreacted t-butanol was distilled off at 65° C. under reduced pressure from the reaction solution to obtain 82.5 g of an oily N-t-butoxycarbonyl-L-phenylalanine methyl ester preparation. The reaction yield was 99.5%. The optical purity of the N-carbonyl-L-phenylalanine methyl ester preparation was 97.5%ee.

The N-carbonyl-L-phenylalanine methyl ester preparation having an optical purity of 97.5%ee was purified by the procedure of Example 1 to obtain a preparation containing its optically active form having an optical purity of 99.5%ee.

EXAMPLE 5

82.6 g (383 mmol) of L-phenylalanine methyl ester hydrochloride was suspended in 351.8 g of toluene to prepare a slurry solution of the L-phenylalanine methyl ester hydrochloride. After the slurry solution was heated to 110° C., the reaction was conducted for 2.5 hours while bubbling phosgene into the slurry solution at a rate of 30 g/hour. After the completion of the reaction, a nitrogen gas was bubbled into the reaction solution at 110° C. at a rate of 45 L/hour for two hours and excess phosgene was removed from the reaction system. Toluene was distilled off at 40° C. under reduced pressure from the reaction solution to obtain 84.8 g of a crude oily N-carbonyl-L-phenylalanine methyl ester preparation. The purity of the N-carbonyl-L-phenylalanine methyl ester preparation was 90.2% and the reaction yield was 96.9%.

A fraction at 150–152° C. was recovered under 1.4 kPa from 84.4 g of the crude N-carbonyl-L-phenylalanine methyl ester preparation by single distillation, thereby to isolate 60.9 g of an N-carbonyl-L-phenylalanine methyl ester.

To 60.9 g of the N-carbonyl-L-phenylalanine methyl ester, 66.0 g of t-butanol was added and the reaction was conducted under reflux for eight hours. Then, the unreacted t-butanol was distilled off at 65° C. under reduced pressure from the reaction solution to obtain 82.5 g of a crude oily N-t-butoxycarbonyl-L-phenylalanine methyl ester. The reaction yield was 99.5%. The optical purity of the N-t-butoxycarbonyl-L-phenylalanine methyl ester preparation was 97.5%ee.

To 82.5 g of the crude oily N-t-butoxycarbonyl-L-phenylalanine methyl ester preparation, 468.0 g of hexane was added, followed by uniform dispersion. As a result, crystals containing its racemic form was precipitated. After the suspension including the crystals of the racemic form was stirred at 20° C. for one hour, the crystal was removed by filtration. The filtrate was concentrated under reduced pressure to obtain 79.2 g of an N-t-butoxycarbonyl-L-phenylalanine methyl ester preparation. Analysis revealed that the optical purity is 99.5%ee. Subsequent analysis also revealed that the optical purity of the removed crystals is 45.6%ee.

EXAMPLE 6

To 1.0 g of an N-t-butoxycarbonyl-L-phenylalanine methyl ester preparation having an optical purity of 97.5%ee obtained in the same manner as in Example 5, 9.0 g of each of the aliphatic hydrocarbons shown in Table 1 was added individually. After stirring at 25° C. for one hour, crystals were removed by filtration. The optical purity of an N-t-butoxycarbonyl-L-phenylalanine methyl ester recovered from the resulting filtrate was determined by analysis to obtain the same results as those in Table 1.

EXAMPLE 7

50.0 g (259 mmol) of a L-phenylalanine ethyl ester hydrochloride was suspended in 220.5 g of toluene to prepare a slurry solution of the L-phenylalanine ethyl ester hydrochloride. After the slurry solution was heated to 110° C., the reaction was conducted for 2.5 hours while bubbling phosgene into the slurry solution at a rate of 20 g/hour. After the completion of the reaction, a nitrogen gas was bubbled into the reaction solution at 110° C. at a rate of 45 L/hour for two hours and excess phosgene was removed from the system. Toluene was distilled off at 40° C. under reduced pressure from the reaction solution to obtain 59.7 g of a crude oily N-carbonyl-L-phenylalanine ethyl ester preparation. The purity of the crude N-carbonyl-L-phenylalanine ethyl ester preparation was 92.2% and the reaction yield was 97.0%.

A fraction at 150–152° C. was recovered under 1.2 kPa from 59.7 g of the crude N-carbonyl-L-phenylalanine ethyl ester preparation by single distillation, thereby to isolate 42.5 g of an N-carbonyl-L-phenylalanine ethyl ester.

To 42.5 g of the N-carbonyl-L-phenylalanine ethyl ester, 43.1 g of t-butanol was added and the reaction was con-ducted at 90° C. for eight hours. Then, the unreacted t-butanol was distilled off at 65° C. under reduced pressure from the reaction solution to obtain 56.3 g of a crude oily N-t-butoxycarbonyl-L-phenylalanine methyl ester preparation. The reaction yield was 99.0%. The optical purity of the crude N-t-butoxycarbonyl-L-phenylalanine ethyl ester preparation was 97.2%ee.

To 56.3 g of the crude oily N-t-butoxycarbonyl-L-phenylalanine ethyl ester preparation, 191.0 g of hexane was added, followed by uniform dispersion. After the resulting suspension was stirred at 2° C. for one hour, crystals were removed by filtration. The optical purity of an N-t-butoxycarbonyl-L-phenylalanine ethyl ester preparation in the resulting filtrate was analyzed. As a result, it was 99.3%ee.

What is claimed is:

1. A purification process for improving an optical purity of an N-t-butoxycarbonylphenylalanine ester preparation, which comprises the steps of:

bringing a crude preparation containing an optically active form of an N-t-butoxycarbonylphenylalanine ester into contact with an aliphatic hydrocarbon, and extracting the optically active form in the crude preparation into the aliphatic hydrocarbon to prepare an extract; and recovering the optically active form from the extract to obtain a purified N-t-butoxycarbonylphenylalanine ester preparation having an improved optical purity.

2. The purification process according to claim 1, wherein the N-t-butoxycarbonylphenylalanine ester is a lower alkyl ester having 1 to 4 carbon atoms.

3. The purification process according to claim 1, wherein the aliphatic hydrocarbon is an aliphatic hydrocarbon having 5 to 8 carbon atoms.

4. A process for preparing an optically active N-t-butoxycarbonylphenylalanine ester, which comprises the steps (1) to (3) of:

(1) reacting a phenylalanine ester salt with phosgene in an organic solvent, thereby to introduce a carbonyl group into an amino group of the phenylalanine ester to prepare an N-carbonylphenylalanine ester;

(2) reacting the N-carbonylphenylalanine ester obtained in the step (1) with t-butanol to prepare a crude N-t-butoxycarbonylphenylalanine ester preparation; and (3) bringing the crude N-t-butoxycarbonylphenylalanine ester preparation obtained in the step (2) into contact with an aliphatic hydrocarbon, extracting an optically active form of an N-t-butoxycarbonylphenylalanine ester into the aliphatic hydrocarbon, and recovering the optically active form from the resulting extract to obtain a purified N-t-butoxycarbonylphenylalanine ester preparation containing the optical active form at an improved optical purity.

5. The preparation process according to claim 4, wherein the N-t-butoxycarbonylphenylalanine ester is a lower alkyl ester having 1 to 4 carbon atoms.

6. The preparation process according to claim 4, wherein the aliphatic hydrocarbon is an aliphatic hydrocarbon having 5 to 8 carbon atoms.

7. The process according to claim 1, wherein a racemic form of the N-t-butoxycarbonylphenylalanine ester is deposited as a crystal during the extraction of the crude preparation.

8. The process according to claim 4, wherein a racemic form of the N-t-butoxycarbonylphenylalanine ester is deposited as a crystal during the extraction of the crude preparation.

* * * * *